United States Patent [19]

Schreiber et al.

[11] Patent Number: 5,757,666
[45] Date of Patent: May 26, 1998

[54] SYSTEM FOR ANALYZING COMPOUNDS CONTAINED LIQUID SAMPLES

[75] Inventors: Joerg Schreiber, Heddesheim; Wilfried Schmid; Hans-Jürgen Kuhr, both of Mannheim, all of Germany

[73] Assignee: Boehringer Mannheim GmbH, Mannheim, Germany

[21] Appl. No.: 728,189

[22] Filed: Oct. 10, 1996

Related U.S. Application Data

[63] Continuation of Ser. No. 231,721, Apr. 22, 1994, abandoned.

[30] Foreign Application Priority Data

Apr. 23, 1993 [DE] Germany ............... 43 13 253.7

[51] Int. Cl.$^6$ .......................................... G01F 15/00
[52] U.S. Cl. ............... 364/509; 364/497; 364/499; 435/805; 435/809; 436/46; 436/47
[58] Field of Search .................. 364/509, 550, 364/551.01, 496–499, 413.08, 413.09, 413.11, 479.01, 479.12, 479.14; 422/68.1, 56–58, 102, 63–65, 104, 82.05; 436/46, 47, 49; 435/805, 808, 809; 73/863, 863.01, 863.81, 863.91, 864, 864.21, 864.31, 864.34, 864.81–864.84, 864.91; 206/204, 205, 569; 215/227, 228; 382/128, 133; 221/135, 79, 149, 186, 197, 198, 289

[56] References Cited

U.S. PATENT DOCUMENTS

| | | | |
|---|---|---|---|
| 3,918,910 | 11/1975 | Soya et al. | 422/66 |
| 4,834,234 | 5/1989 | Sacherer et al. | 206/204 |
| 4,911,344 | 3/1990 | Kahler | 221/135 |
| 5,047,044 | 9/1991 | Smith et al. | 606/182 |
| 5,053,198 | 10/1991 | Quenin | 422/64 |
| 5,084,246 | 1/1992 | Lyman et al. | 435/809 |
| 5,104,811 | 4/1992 | Berger et al. | 436/164 |
| 5,146,793 | 9/1992 | Sgourakes et al. | 73/864.21 |
| 5,281,395 | 1/1994 | Markart et al. | 422/82.05 |
| 5,281,540 | 1/1994 | Merkh et al. | 422/57 |
| 5,311,426 | 5/1994 | Donohue et al. | 364/413.09 |
| 5,320,808 | 6/1994 | Holen et al. | 422/58 |
| 5,425,921 | 6/1995 | Coakley et al. | 422/102 |
| 5,460,968 | 10/1995 | Yoshida et al. | 422/63 |

FOREIGN PATENT DOCUMENTS

| | | |
|---|---|---|
| 271 854 B1 | 6/1988 | European Pat. Off. . |
| 299 517 A2 | 1/1989 | European Pat. Off. . |
| 373 413 A1 | 6/1990 | European Pat. Off. . |
| WO 94/10558 | 5/1994 | WIPO . |

*Primary Examiner*—Emanuel T. Voeltz
*Assistant Examiner*—Hal D. Wachsman
*Attorney, Agent, or Firm*—Nikaido, Marmelstein, Murray & Oram LLP

[57] ABSTRACT

A system for analyzing sample liquids using dry reagents is configured for the determination of clinical parameters. The system including an analysis instrument containing the test elements to carry out the test. Form and design of the test elements are adjusted for use in the analysis system. The system is utilized for analyses where available test elements which are in contact with their environment exhibit a low storage stability.

27 Claims, 6 Drawing Sheets

SYSTEM FOR ANALYZING COMPOUNDS CONTAINED LIQUID SAMPLES

This application is a continuation of application Ser. No. 08/231.721 filed Apr. 22, 1994, now abandoned.

BACKGROUND OF THE INVENTION

1. Field of the Invention

The invention addresses a system for analyzing sample liquids, said system comprising a linear arrangement of test elements, a measuring arrangement for detecting changes occurring on a test element and two or more test elements included within the system. The test elements are provided with a device for protection against moisture.

The invention also comprises storage containers for two or more test elements and test elements whose shape enables sealing against moisture. With the system according to the invention a method of analyzing sample liquids is possible which does not employ liquid reagents.

2. Description of the Related Art

Analysis systems which allow analyzing individual parameters in sample liquids are known from prior art. Especially in the fields of medicine and environmental protection, there exist systems which can also be operated by poorly trained personnel. Instruments which operate without the use of liquid reagents, often also referred to as dry analysis, are usually easy to operate. Instruments for the determination of glucose in blood are known, for example, where the patient applies blood onto a test strip and carries out the measurement in an easy to operate instrument. In prior art analysis systems which use dry reagents, the test elements are provided separately outside the instrument.

Known instruments have an opening, usually a slot, through which the test strips are inserted. Guiding elements ensure proper insertion of the test strip. Since the test strip is manually inserted into the instrument, the latter must have structural design features to ensure the test strip is positioned as desired. This is usually realized by means preventing the test strip from being inserted beyond a given target position. The most common systems are designed for analytical tests which are based on color changes. The detection of the color changes occurring on the test strip is realized most commonly by means of reflectance photometry. A measurement of the transmission is also possible, but requires that the test strips be at least partially transparent. The devices necessary for generating and detecting beams of radiation when using photometric methods are principally known in prior art.

Prior art test strips have a test field and a holding zone to handle the strip. The test field itself may comprise several layers. Test fields for determinations in blood are usually provided with fleece layers to separate cells from serum. Moreover, they also feature layers where the reactions occur or the dosage of the analyte is carried out. A possible design of test strip is, for example, described in patent application EP-A-0271854. The direct formation of a color as a way of detecting an analyte is only possible in rare cases. The detection usually requires a series of chemical and/or biochemical reactions resulting in the formation or degradation of a color. Size and shape of the test field on which a color is formed or degraded must account for manufacturing tolerances of instrument and test element to ensure that a test field of uniform dimensions is available for the measurement. Test elements known in prior art have the form of a strip or a flat rectangular plate. The materials used are paper, special cardboards or plastics. The test field is applied onto said materials either by impregnation or in the form of additional layers. The storage stability of many test elements is drastically reduced by the effect of moisture. Commercially available test elements are, therefore, either individually sealed or, if produced in larger quantities, packed in special containers. Plastic-laminated metal foils, particularly aluminum laminates are usually used for sealing. This type of packaging is used especially for rapid tests which have to be visually evaluated. When a test element is actually used, the sealing is manually removed and the element withdrawn from the package. Test strips which are used repeatedly by one and the same person, for example for the determination of glucose in blood, are usually contained in containers which are impermeable to moisture and, in addition, contain drying agents to absorb any moisture that may have entered the container.

The stability of tablets is also greatly reduced by moisture. Containers with drying agents are also used for tablets, but most of the commercially available tablets is sealed in so-called blister packs.

The actual measurement with known systems for analysis with dry reagents is carried out with the aid of an analysis instrument and separate test strips. The user of a system manually opens a storage container, removes a test strip and closes the storage container again to protect test strips which remain in the container from moisture. Subsequently, a liquid to be analyzed is applied onto the reaction field of the test strip. The test strip is then inserted into the analysis instrument either directly after the application or after a certain incubation time has passed. In some known systems, the sample is applied only after the test strip has been inserted into the instrument. In both procedures, the test strip is positioned in the instrument by the user. To ensure proper positioning, the user inserts a test strip until contact is made with a mechanical barrier.

The measurement is then triggered by pressing a key on the instrument. However, there exist also systems where the measurement is initiated automatically when the test strip is inserted into the instrument. Once the measurement is completed which is indicated on the instrument display the analysis procedure is terminated by manually removing the test strip.

U.S. Pat. No. 4,852,025 discloses a system for determining the concentration of body fluid components involving the use of a processor or CPU, control keys, and a display. Such a system could be utilized with respect to operating elements or keys (4) and display (5) of FIG. 1, or operating elements (33) and display (34) of FIGS. 5 and 7. The disclosure of U.S. Pat. No. 4,852,025 is hereby incorporated by reference for the teaching of such system components therein.

A drawback of systems known in prior art is that instrument and test strips are separated from another. In addition to the actual instrument, the user has to carry at least one additional container. Moreover, a disadvantage of all storage containers for test strips is that all the elements contained therein are brought into contact with moisture when one element is removed. Another disadvantage of existing systems lies in the manual positioning of the test strips by the user which does not completely eliminate improper usage.

SUMMARY OF THE INVENTION

It was, hence, an object of the invention to provide a system for carrying out a number of analytical determinations without introducing individual test strips into the instrument from the outside. The user should also be able to carry out the determination in a reliable manner when the system was stored in the presence of moisture. Further, the test elements should be positioned with the aid of the system such that operating errors are avoided to a largest possible extent.

This object was accomplished in accordance with the invention by a system, which
- is provided with two or more test elements in a linear arrangement,
- is provided with a storage container for the test elements, said container being provided inside the system from which it can also be removed,
- is provided with a measuring arrangement for detecting changes occurring on a test element, and contact pressure devices for sealing the test element against moisture, said means exerting a mechanical pressure onto the storage container.

The system of the invention comprises a measuring instrument and an arrangement of test elements. The measuring instrument is provided with an insertion device for the storage container containing two or more test elements. The test elements can be successively forwarded to the site of measurement. In the instrument, there is a measuring device comprising a radiation source and a radiation receiver. An analysis can be achieved via detectable signals whose strength depends on the concentration of the parameter to be determined in the sample. The expert is familiar with detectable signals suitable for such an analysis, e.g. optical, electrical, or magnetic signals. In a preferred manner, the radiation source emits light in the visible spectrum. It is possible to use radiation sources with a continuous or a discrete spectrum. The emitted beams of radiation can impinge either directly on the test element or be directed through a preceding optical arrangement. The optical arrangement according to the invention can comprise elements such as lenses, mirrors, and also components for reducing certain ranges of the emitted light. These are preferably optical filters. However, grids or prisms for selecting a certain frequency or frequency ranges are also possible.

Some of the light reflected by the test element arrives at the receiver after passing through an optical arrangement. Such an optical arrangement can contain the above described elements. The invention also covers accomplishments where the reflected light directly impinges on the receiver. The receiver can be present in the form of photomultipliers, photodiodes, photovoltaic elements or other sensors known in prior art. The signal emitted by the receiver can be processed either directly or be passed through principally known electrical circuits and then be visualized on a display. The display in accordance with the invention can, for example, be an analog measuring instrument or, preferably, a digital display.

The Instrument can also feature an integrated reading device which reads in data that is characteristic for the test elements used and/or the analysis to be carried out. Such data can, for example, be displayed on the storage container for the test elements or be separately fed to the instrument. Reading devices include barcode readers, magnetic strip readers, and other known devices. The data which is read in can, for example, include the type of test element used, the lot number, the expiration date, and manufacturing-tolerances of test elements. The data can also include the type of analysis to be carried out.

The invention covers storage containers for two or more test elements which comprise both a device for transporting the test elements and a device for sealing test elements against moisture. The system of the invention can, for example, be realized with storage containers for two or more test elements, said containers having an opening which can be closed to exclude moisture by pressing two opposing sides against each other. The system of the invention is characterized by a storage container in which the test elements are stored to be protected from moisture. The test elements are provided in a linear arrangement and are individually protected against moisture. Individual sealing is achieved in that moisture is excluded by applying contact pressure to each test element. Preferably, this mechanical contact pressure unit is provided within the storage container, such that the test elements are also protected against moisture after removal of the storage container from the system. The contact pressure unit can be realized, for example, by means of springs provided in the system and having bodies at one of their ends which fittingly enter a corresponding recess in the test element. A test field, for example, which is present in a circular recess of a test element can be sealed by applying pressure with a semi-spherical element.

Apart from the option of individually sealing the test elements against moisture, it is also possible to seal off the entire storage container in which they are contained. In this case, preferred embodiments are those where sealing is realized by applying pressure onto the opening of the container. It is, hence, advantageous if the container opening or the entire container is made of an elastic material so that the opening can be easily pressed together. Preferred materials include plastics, particularly polyvinyl chloride, polyethylene, polypropylene and Teflon. It is possible to use storage containers which can be refilled once all test elements are used up as well as disposable containers. Transportation of the test elements from the storage container to the site of sample application can be accomplished by means of a mechanical unit. This could be a pushing device, for example, but it is also possible to use the arrangement of the test elements itself for the purpose of transporting the test elements. In a preferred embodiment of the invention, the storage container can be removed from the system.

Storage containers of the invention can also be provided with a corresponding label which can either be attached directly to the container or be provided separately. In the latter case the user must be able to clearly identify it. A storage container can, for example, be provided with a barcode or magnetic strip which is automatically read when the storage container is inserted into the instrument. In another embodiment, storage container and label are provided separately, but are packed together. Identification can then be provided in the form of a strip with the barcode, a chip card, a radio-frequency identification card (RF-ID chip) and other storage possibilities known in the art.

The invention further includes a mechanically linked arrangement of test elements which is provided with determined breaking points such that individual test elements can be removed by breaking them off. In an arrangement of this kind, a used test element can be removed from the arrangement of the remaining test elements by tearing, breaking or snapping it off. Another mechanically linked arrangement proposes to connect the test elements with each other in the same way as the pieces of a jigsaw puzzle are connected. In this type of connection the entire arrangement of test elements can be transported by moving one single test element located outside the storage container. The test element outside the storage container can be removed from the arrangement by moving it perpendicular to the direction of transportation. In a preferred manner, the holding zone of at least one other test element is positioned outside the storage container after the removal of a test element. This test element can then be transported with the aid of said holding zone. While the holding zone is outside the storage container, the moisture-sensitive part of the corresponding test element is located inside the storage container where it is protected from moisture.

Further, the invention also covers test elements whose shape allows sealing of the test field against moisture by means of contact pressure of other elements. Test elements in accordance with the invention are preferably provided with a frame made of a material which exhibits sufficient mechanical stability to allow transportation of the test element in the system of the invention without damaging the test field. Preferred materials include plastics, glass, cardboards and metal. The frame is provided with a recess for the test field and in preferred embodiments, it may be given a shape which renders it fit to be used as a grip or a holder. The frame is mechanically linked to the test field. Preferably, the test field is on one level surrounded by the frame. The test field can be pressed or glued into the frame. If the frame is made of plastic, it is also possible that it is molded or injected around the test field during manufacture. If desired, the test field contains several layers or areas which may serve as sample application zones. In said zones, cells are separated, if necessary, and the reactions occur which cause a detectable change in the presence of a certain analyte. In all other cases, the test field can be provided with embodiments as they are described above with respect to prior art. In accordance with the invention, the test field can be protected against moisture in that the devices in the system together with the frame form a space to contain the respective test field, said space being sealed with respect to the outside. The frame can, for example, be planar or have elevated segments on its surface, so that the test field is sealed when a device, preferably a plate or a stamp is pressed against both the upper and lower sides of the test element. The test element can also be designed such that the test field is provided in a circular recess of the frame. In this case, the access of moisture to the test field can be prevented by pressing a sphere, parts of a sphere, or a conical cylinder onto the circular recess.

With the system of the invention, it is possible to carry out a method of analyzing sample liquids which comprises the following steps:

Transporting a test element with a pushing device from a storage container to the site of measurement Applying the sample liquid onto the test element Detecting a sample-induced change of the test element Calculating the result of the measurement based on the detected change Reading the measurement off a display Ejecting the test element with an arm or a lever.

Moreover, the invention also covers a method of analyzing sample liquids with the following steps Opening a sealing device by taking pressure off the contact pressure device.

Transporting a test element of an arrangement of test element from a storage container to the site of measurement.

Closing the sealing device.

Applying sample liquid onto the test element.

Detecting a sample-induced change of the test element.

Calculating a measurement based on the detected change.

Reading the measurement off a display.

Removing a used test element from the arrangement of test elements.

A user advantage of the system of the invention is that it does not require an external storage device for test strips since it has a system-integrated magazine to contain test elements. Manual transportation of individual test strips from the storage container to the instrument which is necessary in present systems thus becomes superfluous and also reduces the risk of contamination, e.g. by accidentally falling down during transport. Further, in the system of the invention, the test elements themselves can be sufficiently protected from moisture after their removal so that the test elements can be used up in the course of weeks or even months without a significant loss of quality.

A particularly preferred embodiment of the system of the invention can be realized by the following design.

BRIEF DESCRIPTION OF THE DRAWINGS

FIG. 1 shows an analysis system (1), with the top cover (2) being opened. The top cover (2) protects the base of the system from contamination and damage. Said base (3) is provided with integrated operating elements (4) and an integrated display (5).

In FIGS. 2a and 2b the system is shown without the top cover (2). The storage container (6) for test elements is located in the front portion of the system below cover (7). It has approximately the shape of a bar and extends over the larger part of the width of the base. Transportation of the test elements to the site of sample application and measurement is achieved by means of a pushing device (8). Sample application and measurement are carried out at the same site which is located above the measurement opening (10). Below this measurement opening (10), there can be provided an optical unit or, as described above, a radiation source and a receiver. During the measurement, a test element is positioned above the measurement opening (10) and held by an arm (9). The area above the measurement opening (10) can be closed with a protective cap (11). This provides protection from ambient light which would lead to erroneous measurements. If other suitable measuring methods are employed, the measurement could also be carried out without excluding ambient light by means of the protective cap (11). If the system is not in use, the protective cap (11) protects the sensitive measuring area against dust and contamination.

FIGS. 2a and 2b explain how the measurement is carried out. A storage container (6) filled with test elements is laterally inserted into the system. The pushing device (8) is moved toward the measurement opening (10) until a test element comes to rest in the recess of arm (9). Now the protective cap (11) is opened and analyte liquid is applied onto the test field of the test element. In order to carry out the measurement, the protective cap (11) must be closed. The measurement can be initiated either by means of one of the operating elements (4) or it is started automatically by closing the protective cap (11), e.g. controlled by means of a light barrier or a switch which is activated by the protective cap (11). The end of a measurement is visually indicated on the display (5) or acoustically indicated by a tone. The result of the measurement is shown on display (5) and can be stored in the system, if desired. A used test element can be removed from the system by bringing arm (9) into the position shown in FIG. 2b. The test element is automatically released from arm (9). Arm (9) is subsequently moved back into the position shown in FIG. 2a. The system is now ready for a new analytical determination.

FIG. 3 shows a storage container (6) for test elements. On the upper side there is a number of elevated portions (12) onto which pressure is exerted by spheres provided on the base (3) of the system in order to seal the test elements. Under each elevated portion (12) of the storage container (6), there is a test element if the magazine is filled. The storage container has an exit (13) for test elements, which is located next to the measurement opening (10) if the storage container (6) is inserted into the system.

FIG. 4 shows an individual test element (14). Test field (16) is surrounded by a frame (15) where the lower and the upper sides are provided with a circular elevation of material (17) to allow and/or improve protection against moisture.

Figure 1:
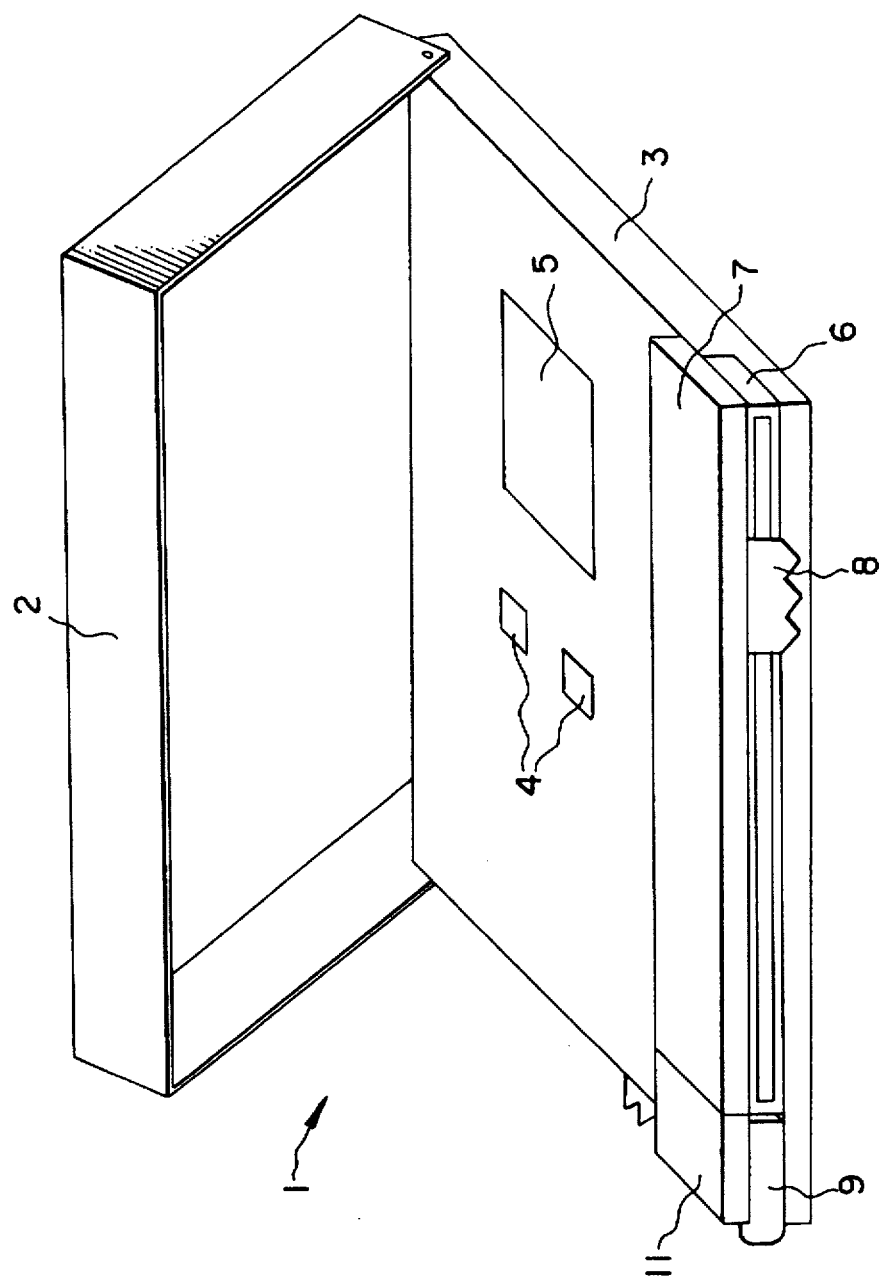
FIG. 1: Analysis system
Figure 2A:
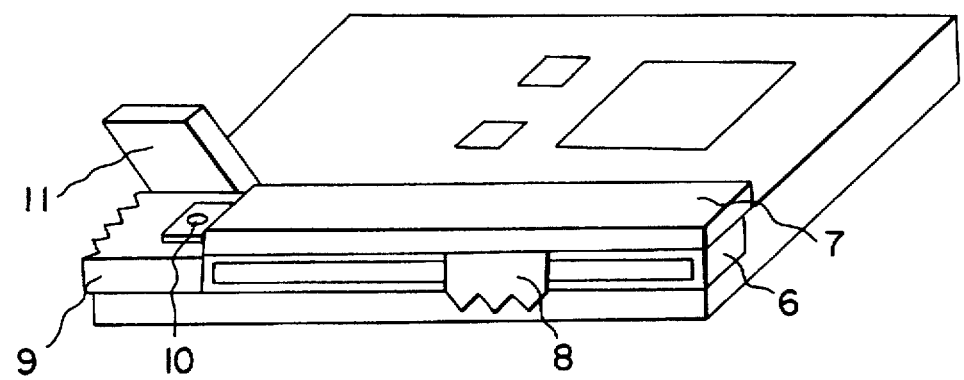
FIGS. 2A and 2B: Analysis system without top cover and with the protective cap being opened
Figure 2B:
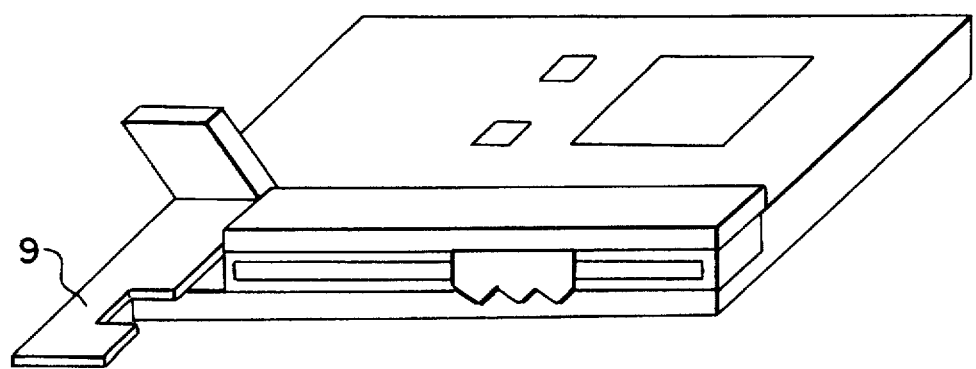
Figure 3:
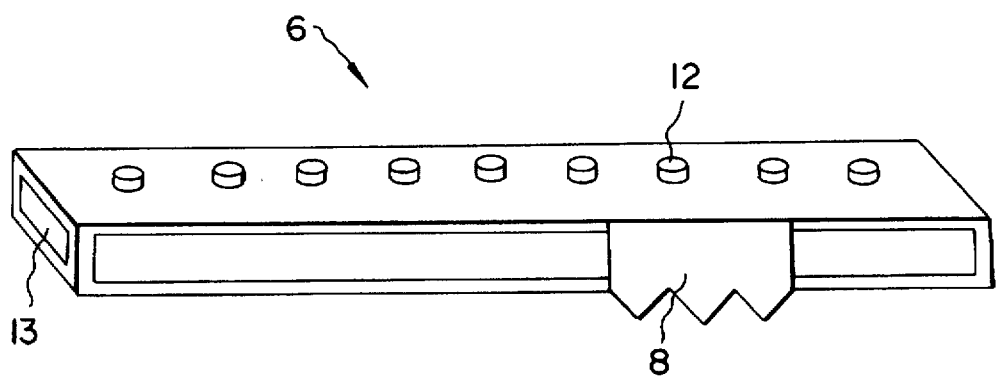
FIG. 3: Storage container for test elements
Figure 4:
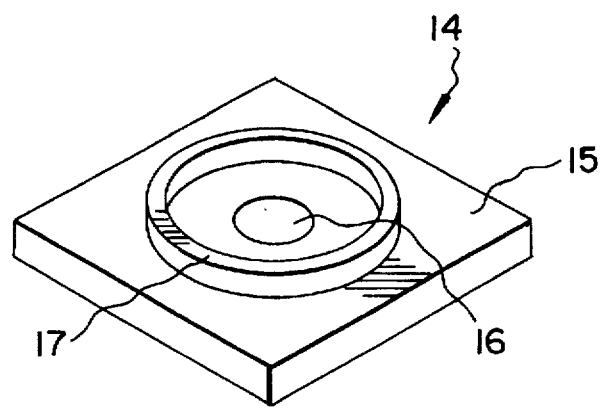
FIG. 4: Test element
Figure 5:
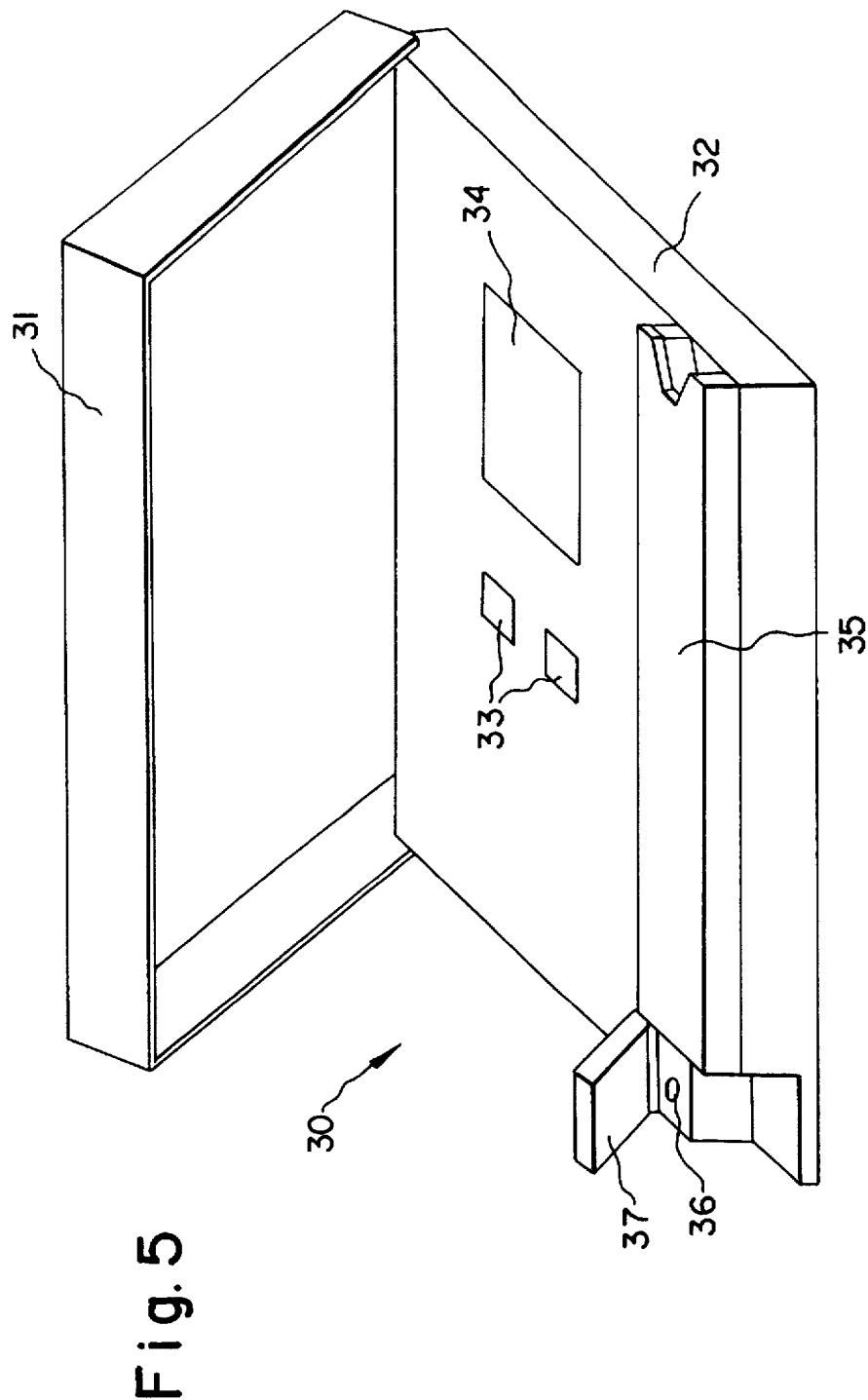
FIG. 5: Analysis system with a sealing device being closed

Another preferred embodiment of the system of the invention is shown in FIG. 5. System (30) has a cover (31) and a base (32). The base (32) is provided with integrated operating elements (33) and an integrated display (34). The storage container for test elements is located below a sealing device (35). In this embodiment, measurement and sample application are also carried out at the same site which is located above the measurement opening (36). During the measurement, a protective cap (37) protects the test element from ambient light.

Figure 6A:
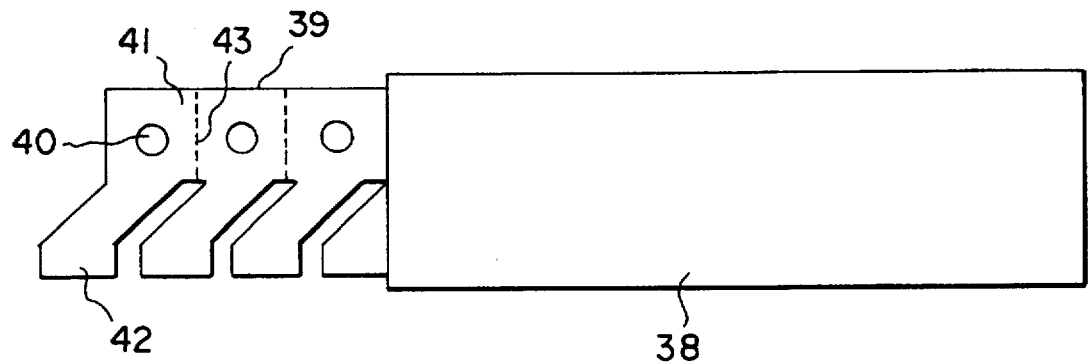
FIGS. 6A and 6B: Storage container for test elements with an arrangement of test elements

FIG. 6a shows a storage container (38) for test elements (39) where the test elements are arranged in accordance with the invention. The storage container (38) has the form of a small box with only one opening to insert the arrangement of test elements (39). The test elements which make up the arrangement of test elements (39) are provided with a test field (40), a frame (41) and a holding portion (42). The test elements are connected to each other, but are provided with designated breaking points (43) to separate the test elements from each other.

Figure 6B:
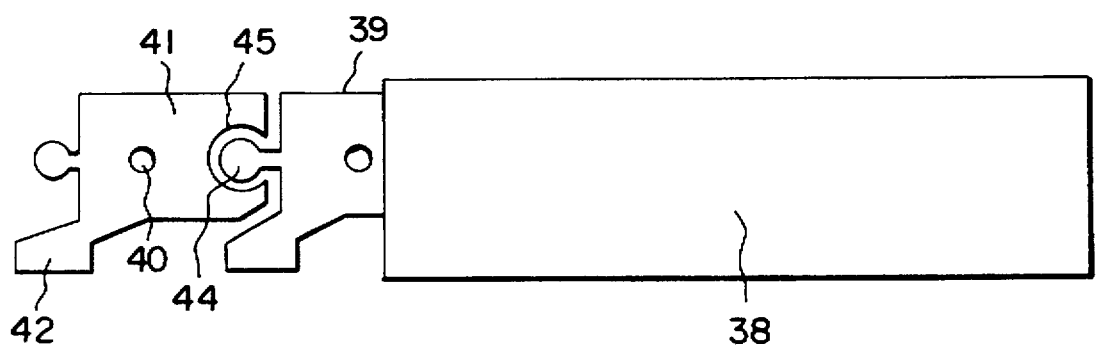

FIG. 6b also shows a storage container (38) for test elements in accordance with the invention. The arrangement corresponds to the one shown in FIG. 6a. However, the test elements (41) are linked to each other like in a jigsaw puzzle. A projection (44) enters a recess (45). The test elements (41) can be pulled out of the storage container (38) without being separated. If, however, a test element is above the measurement opening (36), it will move toward the measurement opening, thus separating the link between projection (44) and recess (45). After the measurement, this test element can then be removed from the system without requiring snapping or breaking off.

Figure 7:
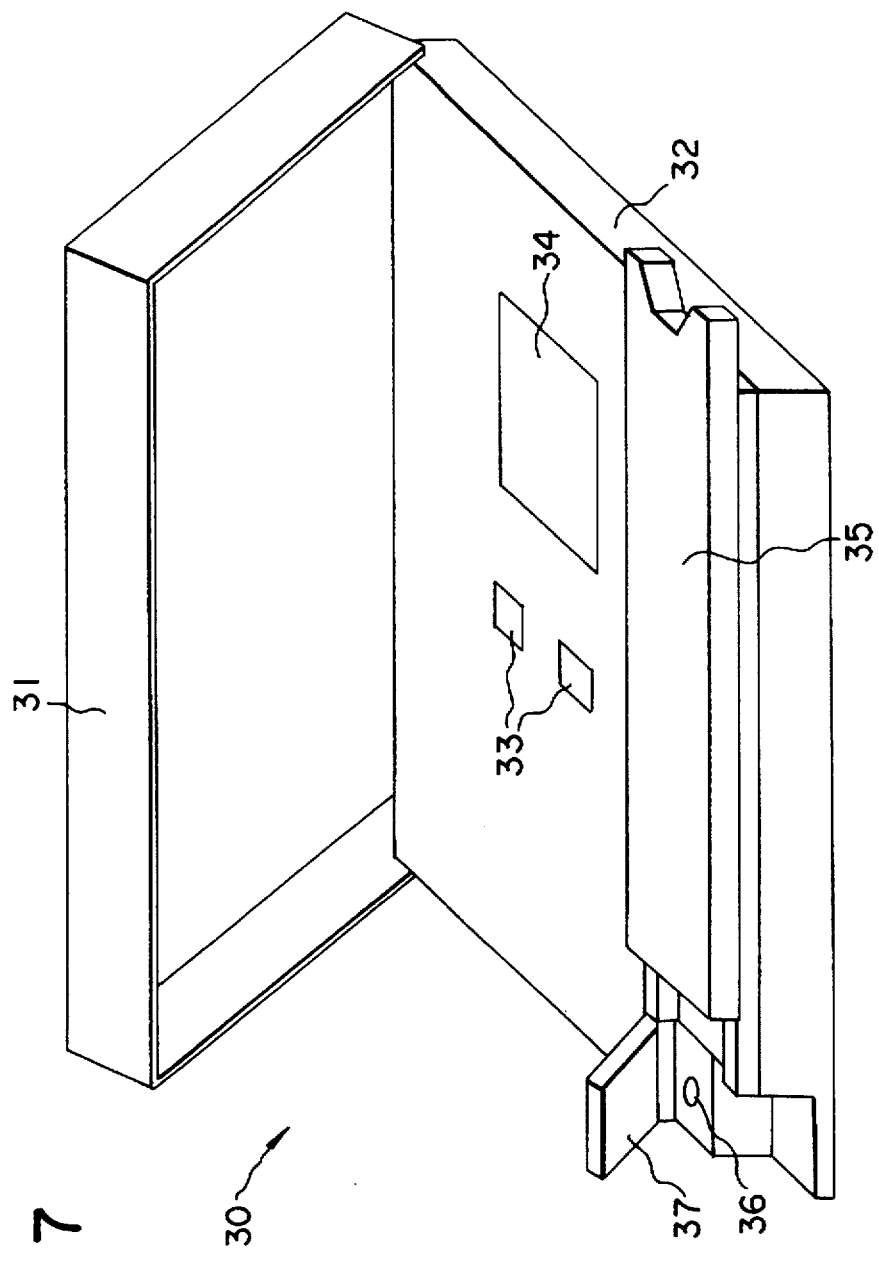
FIG. 7: Analysis system with the sealing device being opened

FIG. 7 explains how the sealing device (35) works. To bring a new test element into measuring position, the bayonet-like attached sealing device (35) is first moved from its position shown in FIG. 5 to the position shown in FIG. 7. This is to release the mechanical pressure from the opening of the storage container. A new test element can then be moved out of the storage container (38) by pulling it at the holding zone (42). If the sealing device (35) is moved back into the position shown in FIG. 5, the sides of the storage container (38) are pressed onto each other. The sealing device (35) thus seals the test elements left in the storage container (38) and in particular the test fields (40) of these elements against moisture.

The measurement according to FIG. 5 is carried out in the following steps:

Opening the sealing device (35).

Inserting a storage container (38) under the sealing device (35).

Removing a test element by pulling at the holding zone (42) until the test field (40) is located above the measurement opening (36).

Closing the sealing device (35).

Applying sample liquid onto the test field (40).

Closing the protective cap (37).

Activating the operating elements (33), if necessary.

Reading the measurement off the display (34).

Opening the protective cap (37).

Breaking off the used test element at the designated point of breaking (43) between the used and the next new test element.

Closing the protective cap (37).

If a storage container has already been inserted into the system, the corresponding operating step in the above listing can be omitted.

When using suitable measurement methods known in prior art, the steps for opening and closing the protective cap (37) which are given in the above listing can be omitted. The measurement can be initiated by activating the operating elements (33) or by detecting the sample application.

REFERENCE LIST

1 System
2 Top cover
3 Base
4 Operating elements
5 Display
6 Storage container for test elements
7 Cover
8 Pushing device
9 Arm
10 Measurement opening
11 Protective cap
12 Elevated portions
13 Exit of storage container
14 Test element
15 Frame of test element
16 Test field
17 Elevation of material of test elements
30 System
31 Cover
32 Base
33 Operating elements
34 Display
35 Sealing device
36 Measurement opening
37 Protective cap
38 Storage container for test elements
39 Arrangement of test elements
40 Test field
41 Frame of test element
42 Holding portion
43 Designated breaking point
44 Projection of a test element
45 Recess of test element

We claim:

1. A system for analyzing a plurality of liquid samples, said system comprising:

a system base;

a plurality of test elements arranged in a linear array, with each test element having a test field which produces a detectable change when contacted by a liquid sample containing a material to be detected;

a storage container containing the plurality of test elements therein, said storage container being removably received in the system base, said storage container having an opening for said test elements to be removed therefrom;

a measuring device attached to said system base for detecting the detectable change produced in a test element of said plurality of test elements;

sealing means attached to said system base, said sealing means comprising a plurality of individual pressing means which seals individual test elements of the plurality of test elements by applying pressure thereto, said pressing means fittingly entering a corresponding recess in corresponding test elements of said plurality of test elements.

2. System of claim 1, wherein the test elements are unattached to one another.

3. A system according to claim 1, wherein each of said individual pressing means has a semi-spherical shape.

4. System of claim 1, wherein the system includes a measurement position of a test element wherein a liquid sample can be applied to the test element, and the detectable change in the test element can be measured by the measuring device.

5. System of claim 1, wherein the system includes a data reading device.

6. System of claim 1, wherein the storage container is elongated and a pushing device moves the test elements along the storage container until an end test element of the test element array reaches a measurement site wherein the test element is in a measuring location to be measured by the measuring device.

7. A method of analyzing a liquid sample by means of the system of claim 1, comprising the steps of:

a) transporting a first test element by means of a pushing device from the storage container to a measurement site;

b) applying the liquid sample to the test field of the first test element at the measurement site;

c) detecting a sample induced change of the test field of the first test element at the measurement site;

d) calculating the result of the measurement based on the detected change;

e) displaying the said result on a display; and f) ejecting the first test element from the system with an arm or a lever.

8. Method of claim 7, including the additional step of detecting data concerning the test elements contained in the storage container, and using such data in the calculating step.

9. Method of claim 8, wherein before step the storage container is inserted into the system base, and the data concerning the test elements is read at the time of storage container insertion.

10. The method of claim 7, wherein at least one other test element is transported within the storage container at the same time that the first test element is transported out of the storage container.

11. A method of analyzing a liquid sample comprising the steps of:

providing a system having a system base with a plurality of test elements arranged in a linear array, with each test element having a test field which produces a detectable change when contacted by a liquid sample containing a material to be detected;

providing a storage container containing the plurality of test elements therein, said storage container being removably received in the system base, said storage container having an opening for the test elements to be removed therefrom;

providing a measuring device attached to the system base for detecting the detectable change produced in a test element of the plurality of test elements;

providing a releasable sealing means attached to the system base, with the releasable sealing means sealing the opening by pressingly engaging the storage container wherein the storage container can be pressed between the sealing means and the system base to seal the opening;

removing pressure from the releasable sealing means to open the opening of the storage container;

transporting the first test element of the test element linear array from the storage container to a measurement site;

closing the opening with the sealing means;

applying liquid sample to a test field of the first test element at the measurement site, the test field producing the detectable change when contacted by a material in the liquid sample;

detecting a sample-induced change of the test field;

calculating a measurement based on the detected change;

displaying the measurement on a display; and removing the used first test element from the test element array.

12. Method of claim 11, including the additional step of detecting data concerning the test elements contained in the storage container, and using such data in the calculating step.

13. Method of claim 12, wherein the storage container is inserted into the system base, and the data concerning the test elements is read at this time of storage container insertion.

14. The method of claim 11, wherein at least one other test element is transported within the storage container at the same time that the first test element is transported out of the storage container.

15. A system for analyzing a plurality of liquid samples, said system comprising:

a system base;

a plurality of test elements arranged in a linear array, with each test element having a test field which produces a detectable change when contacted by a liquid sample containing a material to be detected;

a storage container containing the plurality of test elements therein, said storage container being removably received in the system base, said storage container having an opening for said test elements to be removed therefrom;

a measuring device attached to said system base for detecting the detectable change produced in a test element of said plurality of test elements;

releasable sealing means attached to the system base, said releasable sealing means sealing said opening by pressingly engaging the storage container, wherein the storage container is pressed between the sealing means and the system base to seal the opening.

16. A system as recited in claim 15, wherein said plurality of test elements is configured such that a test element is pressed between opposing sides of the storage container when the sealing means pressingly engages the storage container, whereby the opening is sealed by pressing engagement of the sealing means, the storage container, the test element, and the system base.

17. A system as recited in claim 16, wherein the test elements are removably attached to each other in the linear array.

18. System of claim 15, wherein said releasable sealing means is movable from a closed position wherein the opening in the storage container is sealed to an open position wherein the opening is not sealed.

19. System of claim 18, wherein said releasable sealing means seals the opening in the closed position at an end of the storage container adjacent the opening.

20. System of claim 15, wherein said storage container and said opening are configured for said test elements to be sequentially removed from said opening.

21. System of claim 15, wherein the storage container is elongated and a pushing device moves the test elements along the storage container until and end test element of the test element array reaches a measurement site wherein the test element is in a measuring location to be measured by the measuring device.

22. System of claim 15, wherein the releasable sealing means engages the storage container to press against two opposing sides of the test element to prevent moisture from accessing the test field of a test element.

23. System of claim 15, wherein the test elements are in a mechanically linked arrangement.

24. System of claim 23, wherein the array of test elements is an integral array provided with predetermined breaking points to enable an individual test element located at an end of the array to be separated from the remaining test elements of the array.

25. System of claim 23, wherein the test elements are hooked together.

26. System of claim 15, wherein the system includes a measurement position of a test element wherein a liquid sample can be applied to the test element, and the detectable change in the test element can be measured by the measuring device.

27. System of claim 15, wherein the system includes a data reading device.

* * * * *